United States Patent [19]

Ishizumi et al.

[11] Patent Number: 4,507,303
[45] Date of Patent: Mar. 26, 1985

[54] SUCCINIMIDE DERIVATIVES, COMPOSITIONS AND METHOD OF USE

[75] Inventors: Kikuo Ishizumi, Toyonaka; Fujio Antoku; Yukio Asami, both of Takarazuka, all of Japan

[73] Assignee: Sumitomo Chemical Company, Limited, Osaka, Japan

[21] Appl. No.: 446,047

[22] Filed: Dec. 1, 1982

[30] Foreign Application Priority Data

Dec. 22, 1981 [JP] Japan ................... 56-208379
Jun. 3, 1982 [JP] Japan ................... 57-95763

[51] Int. Cl.³ ............... A61K 31/505; C07D 403/04; C07D 403/14
[52] U.S. Cl. ................... 514/255; 544/230; 544/295; 544/364; 544/372
[58] Field of Search ............. 544/295, 364, 372; 424/251, 250

[56] References Cited

U.S. PATENT DOCUMENTS

| 2,928,846 | 3/1960 | Bavley et al. | 548/411 |
| 3,184,456 | 5/1965 | Clinton et al. | 544/372 |
| 3,398,151 | 8/1968 | Wu | 544/230 |
| 3,717,634 | 2/1973 | Wu et al. | 544/230 |
| 3,850,922 | 11/1974 | Matuo et al. | 544/372 |
| 3,907,801 | 9/1975 | Wu et al. | 544/230 |
| 3,976,776 | 9/1976 | Wu et al. | 424/251 |
| 4,182,763 | 1/1980 | Casten et al. | 424/251 |

OTHER PUBLICATIONS

Journal of Medicinal Chemistry, 1972, vol. 15, No. 5, pp. 477–479, 1972.
Zagidullin, Chemical Abstracts, vol. 81, 3882x, (1974).

Primary Examiner—Glennon H. Hollrah
Assistant Examiner—James H. Turnipseed
Attorney, Agent, or Firm—Birch, Stewart, Kolasch & Birch

[57] ABSTRACT

Succinimide derivatives representable by the following formula:

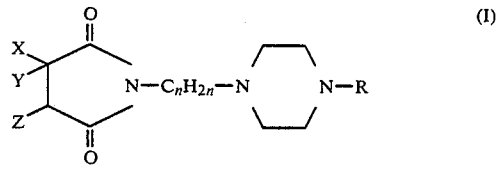

wherein X and Y are combined to form a group of the formula:

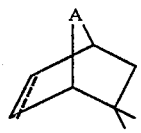

(wherein A is an oxygen atom, a methylene group or an ethylene group and a full line accompanying a broken line ($=\!=\!=$) is a single bond or a double bond) and Z is a hydrogen atom or, X and Z are combined to form a group of the formula:

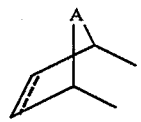

(wherein A and a full line are each as defined above) and Y is a hydrogen atom, R is a phenyl group, optionally substituted with halogen, $C_1$–$C_4$ alkyl, $C_1$–$C_4$ alkoxy or trifluoromethyl, a 2-pyridyl group or a 2-pyrimidinyl group and n is an integer of 3 or 4, and pharmaceutically acceptable acid addition salts thereof, which are useful as antianxious substances.

9 Claims, No Drawings

SUCCINIMIDE DERIVATIVES, COMPOSITIONS AND METHOD OF USE

This invention relates to novel succinimide derivatives. More particularly, it relates to novel succinimide derivatives substituted with piperazinylalkyl group at the imido-nitrogen atom, which have antianxious activity, and processes for preparation thereof and pharmaceutical compositions comprising the same for treatment of an anxiety state.

The succinimide derivatives of this invention can be representable by the following formula:

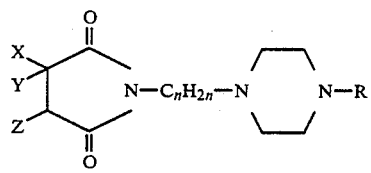
(I)

wherein X and Y are combined to form a group of the formula:

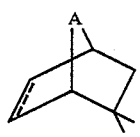

(wherein A is an oxygen atom, a methylene group or an ethylene group and a full line accompanying a broken line (----) is a single bond or a double bond) and Z is a hydrogen atom or, X and Z are combined to form a group of the formula:

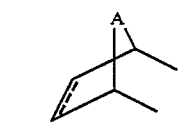

(wherein A and a full line accompanying a broken line are each as defined above) and Y is a hydrogen atom, R is a phenyl group, optionally substituted with halogen, $C_1$-$C_4$ alkyl, $C_1$-$C_4$ alkoxy or trifluoromethyl, a 2-pyridyl group or a 2-pyrimidinyl group and n is an integer of 3 or 4, and pharmaceutically acceptable acid addition salts thereof.

The term and definitions used in this specification are illustrated as follows:

Partial structure ---- is intended to mean both of

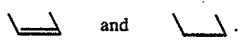 and .

Accordingly, it is to be understood that the compound (I) includes two series of compounds, one of which is represented by the formula:

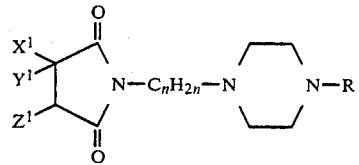
(Ia)

wherein $X^1$ and $Y^1$ are combined to form a group of the formula:

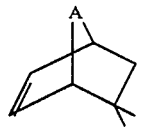

(wherein A is as defined above) and $Z^1$ is a hydrogen atom or, $X^1$ and $Z^1$ are combined to form a group of the formula:

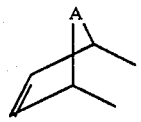

(wherein A is as defined above) and $Y^1$ is a hydrogen atom, and R and n are each as defined above, and the other is represented by the formula:

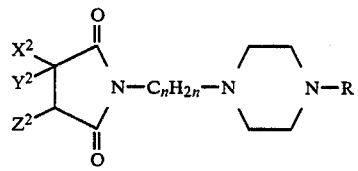
(Ib)

wherein $X^2$ and $Y^2$ are combined to form a group of the formula:

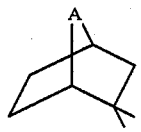

(wherein A is as defined above) and $Z^2$ is a hydrogen atom, or $X^2$ and $Z^2$ are combined to form a group of the formula:

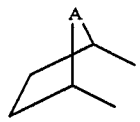

(wherein A is as defined above) and $Y^2$ is a hydrogen atom, and R and n are each as defined above.

When X and Z are combined to form a group of the formula:

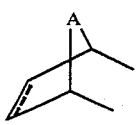

the succinimide derivative (I) has partial structure of the following formula:

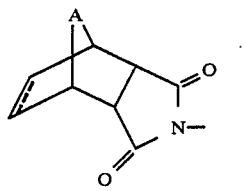

which is intended to mean both of the geometric formulae:

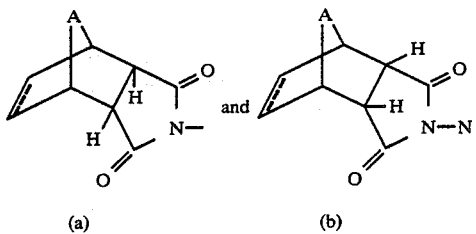

wherein A is as defined above.

When A and are different (i.e. not ethylene simultaneously), the formulae (a) and (b) represent different partial structures. The formula (a) represents a partial structure in which A and the imido group are located on the same side in respect of the six-membered carbocycle, and is referred to as "exo". The formula (b) represents a partial structure in which A and the imido group are located on the different side in respect of the six-membered carbocycle, and is referred to as "endo". It is to be understood that the compound (I) includes both of the "exo" isomer and "endo" isomer, and the mixture of them.

The term "halogen" may include chlorine, bromine, iodine and fluorine. The term "$C_1$-$C_4$ alkyl" may include a residue of straight or branched alkane having 1 to 4 carbon atoms such as methyl, ethyl, propyl, isopropyl, butyl and isobutyl. The term "$C_1$-$C_4$ alkoxy" may include a residue in which straight or branched alkane having 1 to 4 carbon atoms is bonded with a bivalent oxygen such as methoxy, ethoxy, propoxy, isopropoxy and butoxy. The group "—$C_nH_{2n}$—" may include a residue of straight or branched alkylene having 3 or 4 carbon atoms such as trimethylene, methyltrimethylene and tetramethylene.

Preferable compounds in the succinimide derivatives (I) are those represented by the formulae:

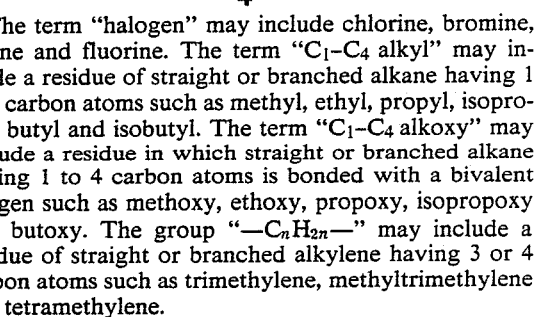

and

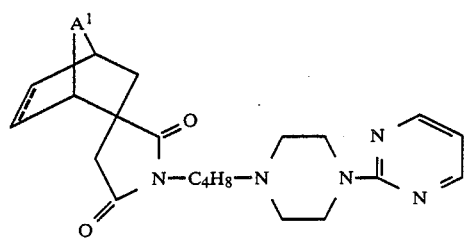

wherein $A^1$ is a methylene group or an ethylene group.

A suitable pharmaceutically acceptable acid addition salt is a conventional non-toxic salt and may be a salt with an inorganic acid such as hydrochloric acid, hydrobromic acid, sulfuric acid, phosphoric acid, etc. or a salt with an organic acid such as acetic acid, propionic acid, butyric acid, tartaric acid, citric acid, maleic acid, fumaric acid, etc.

The succinimide derivatives of this invention can be prepared by processes as shown in the following scheme:

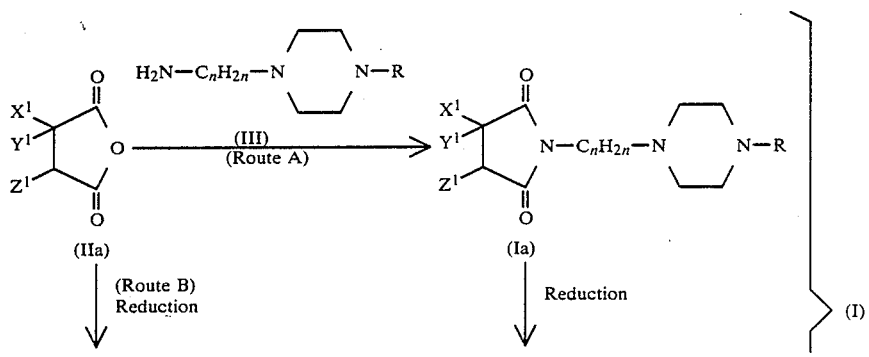

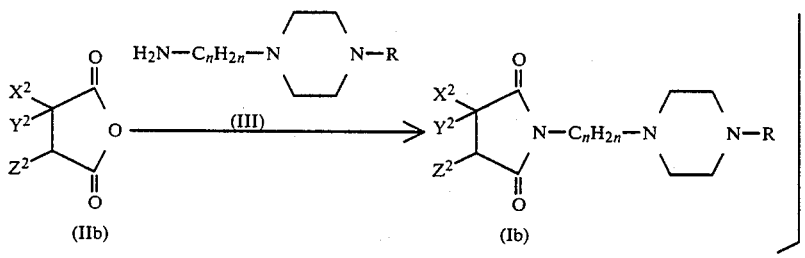

wherein $X^1$, $X^2$, $Y^1$, $Y^2$, $Z^1$, $Z^2$, n and R are each as defined above.

Said processes are explained in details in the following:

Route A

The compound (Ia) can be prepared by reacting the compound (IIa) with the amine (III). The starting compound (IIa) can be prepared by a process reported by T. V. Auken et al. (J.Org.Chem., 23, 626 (1958)) or Inokuma et al. (Japanese Patent Publn. (unexamined) No. 145650/1979).

The reaction is usually carried out by heating the compound (IIa) and the amine (III) in a conventional inert solvent. Suitable solvent may include pyridine and n-butanol.

The reaction includes in its scope the cases that a half-amide compound of the formula:

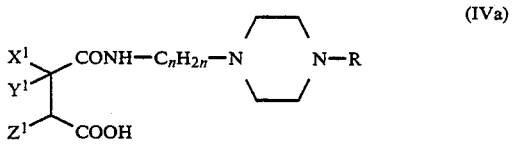

(IVa)

wherein $X^1$, $Y^1$, $Z^1$, R and n are each as defined above is formed. The compound (IVa) takes in some cases a long period of time for cyclization to the compound (Ia). In such case, the cyclization may be easily effected by heating the compound (IVa) in an acetic anhydride. The obtained compound (Ia) may optionally be reduced to the compound (Ib).

The reduction is usually carried out by hydrogenating the compound (Ia) in the presence of a hydrogenation catalyst in a solvent. Suitable hydrogenation catalyst may include conventional ones such as platinum catalyst (e.g. platinum black, platinum dioxide, platinum colloid), palladium catalyst (e.g. palladium black, palladium on carbon, palladium colloid), rhodium catalyst and nickel catalyst (e.g. Raney nickel, nickel oxide). Suitable solvent may include lower alkanol (e.g. methanol, ethanol, isopropanol), water, acetic acid, ethyl acetate, tetrahydrofuran and dioxane. The hydrogenation may be carried out under either atmospheric pressure or increased pressure and at either ordinary temperature or elevated temperature.

Route B

The compound (Ib) can be prepared by reducing the compound (IIa) and then reacting the resultant compound (IIb) with the amine (III).

The reduction of the compound (IIa) to the compound (IIb) and the reaction of the compound (IIb) with the amine (III) may be conducted in a manner similar to that of the reduction of the compound (Ia) to the compound (Ib) and the reaction of the compound (IIa) with the amine (III), respectively.

The reaction of the compound (IIb) with the amine (III) to produce the compound (Ib) includes in its scope the cases that a half-amide compound of the formula:

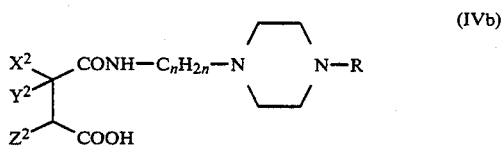

(IVb)

wherein $X^2$, $Y^2$, $Z^2$, R and n are each as defined above is formed as an intermediate, and the compound (IVb) may be imidated to the compound (Ib) in a manner similar to that of the compound (IVa).

Some examples of the compound of the formula (I) are listed below:

N-[4-{4-(2-Pyrimidinyl)-1-piperazinyl}butyl]bicyclo[2.2.1]heptane-2,3-di-exo-carboximide;

N-[4-{4-(2-Pyridyl)-1-piperazinyl}butyl]bicyclo[2.2.1]heptane-2,3-di-exo-carboximide;

N-[4-{4-(2-Chlorophenyl)-1-piperazinyl}butyl]bicyclo[2.2.1]heptane-2,3-di-exo-carboximide;

N-[4-{4-(2-Trifluoromethylphenyl)-1-piperazinyl}butyl]bicyclo[2.2.1]heptane-2,3-di-exo-carboximide;

N-[4-{4-(2-Methylphenyl)-1-piperazinyl}butyl]bicyclo[2.2.1]heptane-2,3-di-exo-carboximide;

N-[4-{4-(2-Methoxyphenyl)-1-piperazinyl}butyl]bicyclo[2.2.1]heptane-2,3-di-exo-carboximide;

N-[3-{4-(2-Pyrimidinyl)-1-piperazinyl}propyl]bicyclo[2.2.1]heptane-2,3-di-exo-carboximide;

N-[3-{4-(2-Pyridyl)-1-piperazinyl}propyl]bicyclo[2.2.1]heptane-2,3-di-exo-carboximide;

N-[3-(4-Phenyl-1-piperazinyl)propyl]bicyclo[2.2.1]heptane-2,3-di-exo-carboximide;

N-[3-{4-(2-Chlorophenyl)-1-piperazinyl}propyl]bicyclo[2.2.1]heptane-2,3-di-exo-carboximide;

N-[4-{4-(2-Pyrimidinyl)-1-piperazinyl}butyl]bicyclo[2.2.1]heptane-2,3-di-endo-carboximide;

N-[4-{4-(2-Pyridyl)-1-piperazinyl}butyl]bicyclo[2.2.1]heptane-2,3-di-endo-carboximide;

N-[3-{4-(2-Pyrimidinyl)-1-piperazinyl}propyl]bicyclo[2.2.1]heptane-2,3-di-endo-carboximide;

N-[4-{4-(2-Pyrimidinyl)-1-piperazinyl}butyl]bicyclo[2.2.2]octane-2,3-dicarboximide;

N-[4-{4-(2-Pyridyl)-1-piperazinyl}butyl]bicyclo[2.2.2]octane-2,3-dicarboximide;

N-[4-{4-(2-Pyrimidinyl)-1-piperazinyl}butyl]-7-oxabicyclo[2.2.1]heptane-2,3-di-exo-carboximide;

N-[4-{4-(2-Pyridyl)-1-piperazinyl}butyl]-7-oxabicyclo[2.2.1]heptane-2,3-di-exo-carboximide;

N-[4-{4-(2-Pyrimidinyl)-1-piperazinyl}butyl]bicyclo[2.2.1]hept-5-ene-2,3-di-exo-carboximide;

N-[4-{4-(2-Pyridyl)-1-piperazinyl}butyl]bicyclo[2.2.1]hept-5-ene-2,3-di-exo-carboximide;

N-[4-{4-(2-Pyrimidinyl)-1-piperazinyl}butyl]bicyclo[2.2.1]hept-5-ene-2,3-di-endo-carboximide;

N-[4-{4-(2-Pyridyl)-1-piperazinyl}butyl]bicyclo[2.2.1]hept-5-ene-2,3-di-endo-carboximide;

N-[4-{4-(2-Pyrimidinyl)-1-piperazinyl}butyl]bicyclo[2.2.2]oct-5-ene-2,3-di-endo-carboximide;

N-[4-{4-(2-Pyridyl)-1-piperazinyl}butyl]bicyclo[2.2.2]oct-5-ene-2,3-di-endo-carboximide;

N-[4-{4-(2-Pyrimidinyl)-1-piperazinyl}butyl]-7-oxabicyclo[2.2.1]hept-5-ene-2,3-di-exo-carboximide;

N-[4-{4-(2-Pyridyl)-1-piperazinyl}butyl]-7-oxabicyclo[2.2.1]hept-5-ene-2,3-di-exo-carboximide;

N-[4-{4-(3-Chlorophenyl)-1-piperazinyl}butyl]bicyclo[2.2.1]heptane-2,3-di-exo-carboximide;

N-[4-{4-(4-Chlorophenyl)-1-piperazinyl}butyl]bicyclo[2.2.1]heptane-2,3-di-exo-carboximide;

N-[4-{4-(2-Pyrimidinyl)-1-piperazinyl}butyl]bicyclo[2.2.1]heptane-2-exo-2-endo-methylenedicarboximide;

N-[4-{4-(2-Pyridyl)-1-piperazinyl}butyl]bicyclo[2.2.1]heptane-2-exo-2-endo-methylenedicarboximide;

N-[4-{4-(2-Chlorophenyl)-1-piperazinyl}butyl]bicyclo[2.2.1]heptane-2-exo-2-endo-methylenedicarboximide;

N-[4-{(4-(2-Trifluoromethylphenyl)-1-piperazinyl}butyl]bicyclo[2.2.1]heptane-2-exo-2-endo-methylenedicarboximide;

N-[4-{4-(2-Methylphenyl)-1-piperazinyl}butyl]bicyclo[2.2.1]heptane-2-exo-2-endo-methylenedicarboximide;

N-[4-{4-(2-Methoxyphenyl)-1-piperazinyl}butyl]bicyclo[2.2.1]heptane-2-exo-2-endo-methylenedicarboximide;

N-[4-(4-Phenylpiperazinyl)butyl]bicyclo[2.2.1]heptane-2-exo-2-endo-methylenedicarboximide;

N-[4-{4-(2-Pyrimidinyl)-1-piperazinyl}butyl]bicyclo[2.2.1]hept-5-ene-2-exo-2-endo-methylenedicarboximide;

N-[4-{4-(2-Pyridyl)-1-piperazinyl}butyl]bicyclo[2.2.1]hept-5-ene-2-exo-2-endo-methylenedicarboximide;

N-[4-{4-(2-Chlorophenyl)-1-piperazinyl}butyl]bicyclo[2.2.1]hept-5-ene-2-exo-2-endo-methylenedicarboximide;

N-[4-{4-(2-Methylphenyl)-1-piperazinyl}butyl]bicyclo[2.2.1]hept-5-ene-2-exo-2-endo-methylenedicarboximide;

N-[4-{4-(2-Methoxyphenyl)-1-piperazinyl}butyl]bicyclo[2.2.1]hept-5-ene-2-exo-2-endo-methylenedicarboximide;

N-[4-(4-Phenylpiperazinyl)butyl]bicyclo[2.2.1]hept-5-ene-2-exo-2-endo-methylenedicarboximide;

N-[3-{4-(2-Pyrimidinyl)-1-piperazinyl}propyl]bicyclo[2.2.1]heptane-2-exo-2-endo-methylenedicarboximide;

N-[3-{4-(2-Pyridyl)-1-piperazinyl}propyl]bicyclo[2.2.1]heptane-2-exo-2-endo-methylenedicarboximide;

N-[3-{4-(2-Chlorophenyl)-1-piperazinyl}propyl]bicyclo[2.2.1]heptane-2-exo-2-endo-methylenedicarboximide;

N-[3-{4-(2-Methylphenyl)-1-piperazinyl}propyl]bicyclo[2.2.1]heptane-2-exo-2-endo-methylenedicarboximide;

N-[3-{4-(2-Methoxyphenyl-1-piperazinyl}propyl]bicyclo[2.2.1]heptane-2-exo-2-endo-methylenedicarboximide;

N-[3-(4-Phenylpiperazinyl)propyl]bicyclo[2.2.1]heptane-2-exo-2-endo-methylenedicarboximide;

N-[3-{4-(2-Pyrimidinyl)-1-piperazinyl}propyl]bicyclo[2.2.1]hept-5-ene-2-exo-2-endo-methylenedicarboximide;

N-[3-{4-(2-Pyridyl)-1-piperazinyl}propyl]bicyclo[2.2.1]hept-5-ene-2-exo-2-endo-methylenedicarboximide;

N-[3-{4-(2-Chlorophenyl)-1-piperazinyl}propyl]bicyclo[2.2.1]hept-5-ene-2-exo-2-endo-methylenedicarboximide;

N-[3-{4-(2-Methylphenyl)-1-piperazinyl}propyl]bicyclo[2.2.1]hept-5-ene-2-exo-2-endo-methylenedicarboximide;

N-[3-{4-(2-Methoxyphenyl)-1-piperazinyl}propyl]bicyclo[2.2.1]hept-5-ene-2-exo-2-endo-methylenedicarboximide;

N-[3-(4-Phenylpiperazinyl)propyl]bicyclo[2.2.1]hept-5-ene-2-exo-2-endo-methylenedicarboximide;

N-[4-{4-(2-Pyrimidinyl)-1-piperazinyl}butyl]bicyclo[2.2.2]octane-2-exo-2-endo-methylenedicarboximide;

N-[4-{4-(2-Pyridyl)-1-piperazinyl}butyl]bicyclo[2.2.2]octane-2-exo-2-endo-methylenedicarboximide;

N-[4-{4-(2-Chlorophenyl)-1-piperazinyl}butyl]bicyclo[2.2.2]octane-2-exo-2-endo-methylenedicarboximide;

N-[4-{4-(2-Trifluoromethylphenyl)-1-piperazinyl}butyl]bicyclo[2.2.2]octane-2-exo-2-endo-methylenedicarboximide;

N-[4-{4-(2-Methylphenyl-1-piperazinyl}butyl]bicyclo[2.2.2]octane-2-exo-2-endo-methylenedicarboximide;

N-[4-{4-(2-Methoxyphenyl)-1-piperazinyl}butyl]bicyclo[2.2.2]octane-2-exo-2-endo-methylenedicarboximide;

N-[4-(4-Phenylpiperazinyl)butyl]bicyclo[2.2.2]octane-2-exo-2-endo-methylenedicarboximide;

N-[4-{4-(2-Pyrimidinyl)-1-piperazinyl}butyl]bicyclo[2.2.2]oct-5-ene-2-exo-2-endo-methylenedicarboximide;

N-[4-{4-(2-Pyridyl)-1-piperazinyl}butyl]bicyclo[2.2.2]oct-5-ene-2-exo-2-endo-methylenedicarboximide;

N-[4-{4-(2-Chlorophenyl)-1-piperazinyl}butyl]bicyclo[2.2.2]oct-5-ene-2-exo-2-endo-methylenedicarboximide;

N-[4-{4-(2-Methylphenyl)-1-piperazinyl}butyl]bicyclo[2.2.2]oct-5-ene-2-exo-2-endo-methylenedicarboximide;

N-[4-{4-(2-Methoxyphenyl)-1-piperazinyl}butyl]bicyclo[2.2.2]oct-5-ene-2-exo-2-endo-methylenedicarboximide;

N-[4-(4-Phenylpiperazinyl)butyl]bicyclo[2.2.2]oct-5-ene-2-exo-2-endo-methylenedicarboximide;

N-[3-{4-(2-Pyrimidinyl)-1-piperazinyl}propyl]bicyclo[2.2.2]octane-2-exo-2-endo-methylenedicarboximide;

N-[3-{4-(2-Pyridyl)-1-piperazinyl}propyl]bicyclo[2.2.2]octane-2-exo-2-endo-methylenedicarboximide;

N-[3-{4-(2-Chlorophenyl)-1-piperazinyl}propyl]bicyclo[2.2.2]octane-2-exo-2-endo-methylenedicarboximide;

N-[3-{4-(2-Methylphenyl)-1-piperazinyl}propyl]bicyclo[2.2.2]octane-2-exo-2-endo-methylenedicarboximide;

N-[3-{4-(2-Methoxyphenyl)-1-piperazinyl}propyl]bicyclo[2.2.2]octane-2-exo-2-endo-methylenedicarboximide;

N-[3-(4-Phenylpiperazinyl)propyl]bicyclo[2.2.2]octane-2-exo-2-endo-methylenedicarboximide;

N-[3-{4-(2-Pyrimidinyl)-1-piperazinyl}propyl]bicyclo[2.2.2]oct-5-ene-2-exo-2-endo-methylenedicarboximide;

N-[3-{4-(2-Pyridyl)-1-piperazinyl}propyl]bicyclo[2.2.2]oct-5-ene-2-exo-2-endo-methylenedicarboximide;

N-[3-{4-(2-Chlorophenyl)-1-piperazinyl}propyl]bicyclo[2.2.2]oct-5-ene-2-exo-2-endo-methylenedicarboximide;

N-[3-{4-(2-Methylphenyl)-1-piperazinyl}propyl]bicyclo[2.2.2]oct-5-ene-2-exo-2-endo-methylenedicarboximide;

N-[3-{4-(2-Methoxyphenyl)-1-piperazinyl}propyl]bicyclo[2.2.2]oct-5-ene-2-exo-2-endo-methylenedicarboximide;

N-[3-(4-Phenylpiperazinyl)propyl]bicyclo[2.2.2]oct-5-ene-2-exo-2-endo-methylenedicarboximide; etc.

The antianxious activity of the succinimide derivative according to the invention could be proved by anti-conflict test. The anti-conflict test was carried out according to the process of Geller and Seifter [Psychopharmacologia, 1, 482 (1960)].

Hungry male rats (Kitayama) of Wistar strain which were previously trained to take feed by leverig were negatively reinforced by receiving an electric shock on levering. As the result, the rats fall into conflict and stopped to levering. When antianxiety substance was administered to the rats, the rats reopened the levering despite of receiving the electric shock. Frequency of the levering under the electric shock was used for an indication of anti-conflict activity or antianxious activity of a test substance. The test substances were administered intraperitoneally to the rats. Tests were carried out while the activity of the substances were at a maximum. The known antianxiety drug "Diazepam" was used for the control. Each dose of 2 mg/kg (i.p.) of N-[4-{4-(2-pyrimidinyl)-1-piperazinyl}butyl]bicyclo[2.2.1]heptane-2-exo-2-endo-methylenedicarboximide hydrochloride (Compound A), N-[4-{4-(2-pyrimidinyl)-1-piperadinyl}butyl]bicyclo[2.2.2]octane-2-exo-2-endo-methylenedicarboximide hydrochloride (Compound B) or N-[4-{4-(2-pyrimidinyl)-1-piperazinyl}butyl]bicyclo[2.2.1]heptane-2,3-di-exo-carboximide hydrochloride (Compound C) had an approximately equal anti-conflict activity or antianxiety activity to 1 mg/kg (i.p.) of Diazepam, and afforded no substantial influence on the general behavior.

Further, none of the compounds (A), (B) and (C) showed any significant effect at a dose of 100 mg/kg (per os) on hexobarbital anesthesia which is an indication of depressing side effect such as sleepiness, while Diazepam reinforced the anesthesia significantly. It was proved from these results that the compounds (A), (B) and (C) are selective antianxiety drugs with less central nervous side effects.

For therapeutic administration, the compound (I) or the salt thereof is used in the form of conventional pharmaceutical preparations suitable for oral administration, for example, tablet, capsule, syrup, suspension, etc., or those suitable for parenteral administration, for example, solution, emulsion, suspension, etc. for injection, or suppository for rectal administration. If needed, there may be included in the above preparations buffers, solubilizers, isotonizers, etc.

While the dosage of the compound (I) may vary from and also depend upon the degree of the infection, age and weight of patient and dosage forms, the active compound can be, in general, administered to adult in an amount between 1 mg and 300 mg, preferably 5 mg and 100 mg per day in single dose or divided doses.

The invention will now be further illustrated by means of the following Examples, which are not, however, intended to limit the scope of the invention.

EXAMPLE 1

A mixture of norbornane-2,3-di-endo-carboxylic anhydride (500 mg, 3 mmol), 1-(4-aminobutyl)-4-(2-pyrimidinyl)piperazine (708 mg, 3 mmol) and pyridine (12.1 ml) was refluxed for 5 hours. The solvent was removed from the mixture under reduced pressure. The residue was purified by silica gel chromatography using chloroform as an eluent. The oily substance obtained was treated with 6% hydrogen chloride/isopropanol. The solvent was removed and the residue was recrystalized from isopropanol to give N-[4-{4-(2-pyrimidinyl)-1-piperazinyl}butyl]bicyclo[2.2.1]heptane-2,3-di-endo-carboximide hydrochloride (920 mg, 67.2 %). M.P., 202°–203° C.

EXAMPLE 2

A mixture of norbornane-2,3-di-exo-carboxylic anhydride (636 mg, 3.8 mmol), 1-(4-aminobutyl)-4-(2-pyrimidinyl)piperazine (900 mg, 3.8 mmol) and pyridine (15.4 ml) was refluxed for 11 hours. Then, the mixture was post-treated in a manner similar to that in Example 1 to give N-[4-{4-(2-pyrimidinyl)-1-piperazinyl}butyl]bicyclo[2.2.1]heptane-2,3-di-exo-carboximide hydrochloride (from isopropanol). M.P., 227°–229° C.

EXAMPLE 3

A mixture of bicyclo[2.2.2]octane-2,3-dicarboxylic anhydride (541 mg, 3 mmol), 1-(4-aminobutyl)-4-(2-pyrimidinyl)piperazine (708 mg, 3 mmol) and pyridine (12.1 ml) was refluxed for 10 hours. The solvent was removed from the mixture under reduced pressure. The residue was extracted with chloroform and water. The chloroform layer was dried over anhydrous sodium sulfate and concentrated under reduced pressure to give crude crystals (1 g), which were treated with 6% hydrogen chloride/isopropanol. The solvent was removed to give N-[4-{4-(2-pyrimidinyl)-1-piperazinyl}butyl]bicyclo[2.2.2]octane-2,3-dicarboximide hydrochloride (from ethanol). M.P., 198°–200° C.

EXAMPLE 4

A mixture of 7-oxabicyclo[2.2.1]heptane-2,3-di-exo-carboxylic anhydride (1 g, 5.95 mmol), 1-(4-aminobutyl)-4-(2-pyrimidinyl)piperazine (1.4 g, 5.95 mmol) and pyridine (23.9 ml) was refluxed for 12 hours. Then, the mixture was post-treated in a manner similar to that in Example 1 to give N-[4-{4-(2-pyrimidinyl)-1-piperazinyl}butyl]-7-oxabicyclo[2.2.1]heptane-2,3-di-exo-carboximide hydrochloride (from isopropanol). M.P., 210°–213° C.

EXAMPLE 5

A mixture of bicyclo[2.2.1]hept-5-ene-2,3-di-exo-carboxylic anhydride (2.2 g, 13.56 mmol), 1-(3-aminopropyl)-4-(2-pyrimidinyl)piperazine (3 g, 13.56 mmol) and pyridine (53 ml) was refluxed for 7 hours. The solvent was removed from the mixture under reduced pressure. The residue was dissolved in chloroform and filtered through a pad of silica gel. The filtrate was concentrated under reduced pressure to give crystals (3.91 g, 78%), which were treated with 5% hydrogen chloride/isopropanol. The solvent was removed and the residue was recrystallized from isopropanol to give N-[3-{4-(2-pyrimidinyl)-1-piperazinyl}propyl]bicyclo[2.2.1]hept-5-ene-2,3-di-exo-carboximide hydrochloride. M.P., 209°–212° C.

EXAMPLE 6

A mixture of N-[3-{4-(2-pyrimidinyl)-1-piperazinyl}propyl]bicyclo[2.2.1]hept-5-ene-2,3-di-exo-carboximide (2.7 g, 7.35 mmol), 5% palladium on carbon (270 mg) and tetrahydrofuran (27 ml) was hydrogenated for 2 hours. The mixture was filtered and the filtrate was concentrated under reduced pressure to give crude crystals, which were treated with 5% hydrogen chloride/isopropanol. The solvent was removed and the residue was recrystallized from ethanol/isopropanol to give N-[3-{4-(2-pyrimidinyl)-1-piperazinyl}propyl]bicyclo[2.2.1]heptane-2,3-di-exo-carboximide hydrochloride. M.P. 216°–217° C.

EXAMPLE 7

A mixture of bicyclo[2.2.1]hept-5-ene-2,3-di-exo-carboxylic anhydride (2.4 g, 14.5 mmol), 1-(3-aminopropyl)-4-(2-pyridyl)piperazine (3.2 g, 14.5 mmol) and pyridine (58.2 ml) was refluxed for 6 hours. The solvent was removed from the mixture under reduced pressure. Acetic anhydride (58.2 ml) was added to the residue and the mixture was refluxed for 30 minutes. Again, the solvent was removed from the mixture and the residue was purified by silica gel chromatography using chloroform as an eluent. The oily substance obtained was treated with 15% hydrogen chloride/isopropanol. The solvent was removed and the residue was recrystallized to give N-[3-{4-(2-pyridyl)-1-piperazinyl}propyl]bicyclo[2.2.1]hept-5-ene-2,3-di-exo-carboximide hydrochloride. M.P., 248°–250° C.

EXAMPLE 8

A mixture of N-[3-{4-(2-pyridyl)-1-piperazinyl}propyl]bicyclo[2.2.1]hept-5-ene-2,3-di-exo-carboximide hydrochloride (3.8 g, 10.3 mmol), 5% palladium on carbon (380 mg) and methanol (38 ml) was hydrogenated for 6 hours. Then, the mixture was treated in a manner similar to that in Example 6 to give N-[3-{4-(2-pyridyl)-1-piperazinyl}propyl]bicyclo[2.2.1]heptane-2,3-di-exo-carboximide hydrochloride (from isopropanol). M.P., 254°–256° C.

EXAMPLE 9

A mixture of bicyclo[2.2.1]hept-5-ene-2,3-bi-exo-carboxylic anhydride (1.5 g, 9.03 mmol), 1-(3-aminopropyl)-4-phenylpiperazine (2 g, 9.03 mmol) and pyridine (36 ml) was refluxed for 7 hours. The solvent was removed from the mixture to give crude crystals (3.6 g). The crude crystals were dissolved in chloroform and treated with activated carbon (72 mg) and silica gel (7.1 g) at room temperature for 1 hour. The mixture was filtered and the filtrate was concentrated under reduced pressure. The residue was treated with 15% hydrogen chloride/isopropanol. The solvent was removed to give N-[3-(4-phenyl-1-piperazinyl)propyl]bicyclo[2.2.1]heptane-2,3-di-exo-carboximide hydrochloride. M.P., 245°–248° C.

EXAMPLE 10

A mixture of bicyclo[2.2.1]hept-5-ene-2,3-di-exo-carboxylic anhydride (1.9 g, 11.8 mmol), 1-(3-aminopropyl)-4-(2-chlorophenyl)piperazine (3 g, 11.8 mmol) and pyridine (47.4 ml) was refluxed for 7 hours. Then, the mixture was post-treated in a manner similar to that in Example 9 to give N-[3-{4-(2-chlorophenyl)-1-piperazinyl}propyl]bicyclo[2.2.1]hept-5-ene-2,3-di-exo-carboximide hydrochloride. M.P., 204°–206° C.

EXAMPLE 11

A mixture of N-[3-{4-(2-chlorophenyl)-1-piperazinyl}propyl]bicyclo[2.2.1]hept-5-ene-2,3-di-exo-carboximide (2 g, 5 mmol), 5% palladium on carbon (200 g) and tetrahydrofuran (20 ml) was hydrogenated for 6 hours. Then, the mixture was post-treated in a manner similar to that in Example 6 to give N-[3-{4-(2-chlorophenyl)-1-piperazinyl}propyl]bicyclo[2.2.1]heptane-2,3-di-exo-carboximide hydrochloride. M.P., 207°–209° C.

EXAMPLE 12

A mixture of bicyclo[2.2.1]hept-5-ene-2,3-di-endo-carboxylic anhydride (1.76 g, 11 mmol), 1-(3-aminopropyl)-4-(2-pyrimidinyl)piperazine (2.37 g, 11 mmol) and pyridine (43 ml) was refluxed for 13 hours. Then, the mixture was post-treated in a manner similar to that in Example 1 to give N-[3-{4-(2-pyrimidinyl)-1-piperazinyl}propyl]bicyclo[2.2.1]hept-5-ene-2,3-di-endo-carboximide hydrochloride (from isopropanol). M.P., 244°–245.5° C.

EXAMPLE 13

A mixture of N-[3-{4-(2-pyrimidinyl)-1-piperazinyl}propyl]bicyclo[2.2.1]hept-5-ene-2,3-di-endo-carboximide (3.4 g, 9.25 mmol), 5% palladium on carbon (340 mg) and tetrahydrofuran (34 ml) was hydrogenated for 3 hours. Then, the mixture was post-treated in a manner similar to that in Example 6 to give N-[3-{4-(2-pyrimidinyl)-1-piperazinyl}propyl]bicyclo[2.2.1]heptane-2,3-di-endo-carboximide hydrochloride (from isopropanol). M.P., 228°–230° C.

EXAMPLE 14

A mixture of bicyclo[2.2.1]heptane-2-exo-2-endo-methylenedicarboxylic anhydride (765 mg, 4.25 mmol), 1-(4-aminobutyl)-4-(2-pyrimidinyl)piperazine (1 g, 4.25 mmol) and pyridine (17.1 ml) was refluxed for 6 hours. Then, the solvent was removed from the mixture under reduced pressure and the residue was purified by silica gel chromatography using chloroform as an eluent. The oily substance obtained was treated with 15% hydrogen chloride/isopropanol to give N-[4-{4-(2-pyrimidinyl)-1-piperazinyl}butyl]bicyclo[2.2.1]heptane-2-exo-2-endo-methylenedicarboximide hydrochloride. M.P., 230°–235° C.

EXAMPLE 15

A mixture of bicyclo[2.2.1]heptane-2-exo-2-endo-methylenedicarboxylic anhydride (1.63 g, 9.04 mmol), 1-(3-aminopropyl)-4-(2-pyrimidinyl)piperazine (2 g, 9.04 mmol) and n-butanol (20 ml) was refluxed for 9¾ hours. Then, the mixture was post-treated in the similar manner as that in Example 14 except that 5% hydrogen chloride was used in place of 15% hydrogen chloride to give N-[3-{4-(2-pyrimidinyl-1-piperazinyl}propyl]bicyclo[2.2.1]heptane-2-exo-2-endo-methylenedicarboximide hydrochloride (from isopropanol) (1.9 g, 46.3%). M.P., 199°–202° C.

EXAMPLE 16

A mixture of bicyclo[2.2.1]heptane-2-exo-2-endo-methylenedicarboxylic anhydride (1.64 g, 9.08 mmol), 1-(3-aminopropyl)-4-(2-pyridyl)piperazine (2 g, 9.08 mmol) and n-butanol (20 ml) was refluxed for 6 hours. Then, the mixture was post-treated in the similar manner as that in Example 14 except that 5% hydrogen chloride was used in place of 15% hydrogen chloride to give N-[3-{4-(2-pyridyl)-1-piperazinyl}propyl]bicyclo[2.2.1]heptane-2-exo-2-endo-methylenedicarboximide hydrochloride (from ethanol/isopropanol) (2.9 g, 70.7%). M.P., 235°–239° C.

EXAMPLE 17

A mixture of bicyclo[2.2.1]heptane-2-exo-2-endo-methylenedicarboxylic anhydride (1.64 g, 9.08 mmol), 1-(3-aminopropyl)-4-phenylpiperazine (2 g, 9.08 mmol) and n-butanol (20 ml) was refluxed for 8 1/6 hours. Then, the mixture was post-treated in the similar manner as that in Example 14 except that 5% hydrogen chloride was used in place of 15% hydrogen chloride to give N-[3-{4-(2-phenylpiperazinyl}propyl]bicyclo[2.2.1]heptane-2-exo-2-endo-methylenedicarboximide hydrochloride (from isopropanol) (2.1 g, 51.2%). M.P., 229°–234° C.

EXAMPLE 18

A mixture of bicyclo[2.2.1]heptane-2-exo-2-endo-methylenedicarboxylic anhydride (1.07 g, 5.91 mmol), 1-(3-aminopropyl)-4-(2-chlorophenyl)piperazine (1.5 g, 5.91 mmol) and n-butanol (15 ml) was refluxed for 6.5 hours. Then, the mixture was post-treated in the similar manner as that in Example 14 except that 5% hydrogen chloride was used in place of 15% hydrogen chloride to give N-[3-{4-(2-chlorophenyl)-1-piperazinyl}propyl]-bicyclo[2.2.1]heptane-2-exo-2-endo-methylenedicarboximide hydrochloride (from isopropanol) (1.39 g, 51.5%). M.P., 220°–221° C.

EXAMPLE 19

A mixture of bicyclo[2.2.2]oct-5-ene-2-exo-2-endo-methylenedicarboxylic anhydride (1.6 g, 8.07 mmol), 1-(4-aminobutyl)-4-(2-pyrimidinyl)piperazine (1.9 g, 8.07 mmol) and n-butanol (19 ml) was refluxed for 6 hours. The solvent was removed from the mixture under reduced pressure and the residue was purified by silica gel chromatography using chloroform as an eluent to give an oily substance (2.8 g, 84.9%). The oily substance (500 mg) was treated with 5% hydrogen chloride/isopropanol and recrystallized from isopropanol to give N-[4-{4-(2-pyrimidinyl)-1-piperazinyl}butyl]bicyclo[2.2.1]oct-5-ene-2-exo-2-endo-methylenedicarboximide hydrochloride 340 mg). M.P., 202°–206° C.

EXAMPLE 20

A mixture of N-[4-{4-(2-pyrimidinyl)-1-piperazinyl}butyl]bicyclo[2.2.2]oct-5-ene-2-exo-2-endo-methylenedicarboximide (2.3 g, 5.62 mmol), 5% palladium on carbon (690 mg) and tetrahydrofuran (23 ml) was hydrogenated at an internal temperature of 50°–60° C. for 5 5/6 hours. Floating matter was removed by filtration and the filtrate was concentrated under reduced pressure. The residue was treated with 5% hydrogen chloride/isopropanol and recrystallized from isopropanol to give N-[4-{4-(2-pyrimidinyl)-1-piperazinyl}butyl]bicyclo[2.2.2]octane-2-exo-2-endo-methylenedicarboximide hydrochloride (780 mg, 28.7%). M.P., 245°–247° C.

EXAMPLE 21

A mixture of bicyclo[2.2.2]octane-2-exo-2-endo-methylenedicarboxylic anhydride (725 mg, 3.73 mmol), 1-(4-aminobutyl)-4-(2-chlorophenyl)piperazine (1 g, 3.73 mmol) and n-butanol (10 ml) was refluxed for 1.5 hours. The solvent was removed from the mixture under reduced pressure and the residue was purified by silica gel chromatography using chloroform as an eluent. The oily substance obtained was treated with 5% hydrogen chloride/isopropanol and recrystallized from isopropanol/ether to give N-[4-{4-(2-chlorophenyl)-1-piperazinyl}butyl]bicyclo[2.2.2]octane-2-exo-2-endo-methylenedicarboximide hydrochloride (970 mg, 50.3%). M.P., 203°–204° C.

EXAMPLE 22

A mixture of bicyclo[2.2.2]octane-2-exo-2-endo-methylenedicarboxylic anhydride (600 mg, 3.09 mmol), 1-(3-aminopropyl)-4-(2-pyrimidinyl)piperazine (684 mg, 3.09 mmol) and n-butanol (6.8 ml) was refluxed for 5 hours. Then, the mixture was treated in a similar manner to that in Example 21 to give N-[3-{4-(2-pyrimidinyl)-1-piperazinyl}propyl]bicyclo[2.2.2]octane-2-exo-2-endo-methylenedicarboximide hydrochloride (from isopropanol) (1.0 g, 66.2%). M.P., 201°–203° C.

EXAMPLE 23

A mixture of bicyclo[2.2.2]octane-2-exo-2-endo-methylenedicarboxylic anhydride (600 mg, 3.09 mmol), 1-(3-aminopropyl)-4-(2-pyridyl)piperazine (681 mg, 3.09 mmol) and n-butanol (6.8 ml) was refluxed for 5 hours. Then, the mixture was treated in a similar manner to that in Example 21 to give N-[3-{4-(2-pyridyl)-1-piperazinyl}propyl]bicyclo[2.2.2]octane-2-exo-2-endo-methylenedicarboximide hydrochloride (from isopropanol) (940 mg, 64.8%). M.P., 214°–215° C.

EXAMPLE 24

A mixture of bicyclo[2.2.2]octane-2-exo-2-endo-methylenedicarboxylic anhydride (600 mg, 3.09 mmol), 1-(3-aminopropyl)-4-phenylpiperazine (678 mg, 3.09 mmol) and n-butanol (6.8 ml) was refluxed for 3 1/6 hours. Then, the mixture was treated in a similar manner to that in Example 21 to give N-[3-{4-(phenylpiperazinyl)}propyl]bicyclo[2.2.2]octane-2-exo-2-endo-methylenedicarboximide hydrochloride (from methanol/ethanol) (880 mg, 60.7%). M.P., 233°–235° C.

What is claimed is:

1. A succinimide derivative of the formula:

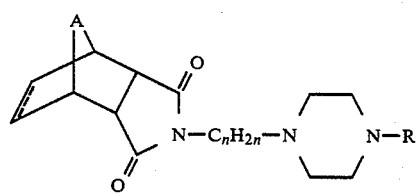

wherein A is an oxygen atom, a methylene group or an ethylene group and a full line accompanying a broken line (═══) is a single bond or a double bond, R is a phenyl group, optionally substituted with halogen, $C_1$–$C_4$ alkyl, $C_1$–$C_4$ alkoxy or trifluoromethyl, a 2-pyridyl group or a 2-pyrimidinyl group and n is an integer of 3 or 4, or a pharmaceutically acceptable acid addition salt thereof.

2. The succinimide derivative as claimed in claim 1, which is a compound of the formula:

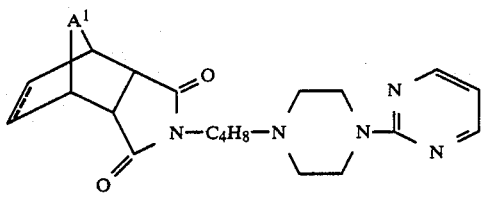

wherein $A^1$ is a methylene group or an ethylene group and the full line accompanying a broken line is as defined in claim 1.

3. The succinimide derivative as claimed in claim 1, which is N-[4-{4-(2-pyrimidinyl)-1-piperazinyl}butyl]-bicyclo[2.2.1]heptane-2,3,di-exo-carboximide or a pharmaceutically acceptable acid addition salt thereof.

4. The succinimide derivative as claimed in claim 1, which is N-[4-{4-(2-pyrimidinyl)-1-piperazinyl}butyl]-bicyclo[2.2.1]heptane-2,3-di-endo-carboximide or a pharmaceutically acceptable acid addition salt thereof.

5. The succinimide derivative as claimed in claim 1, which is N-[4-{4-(2-pyrimidinyl)-1-piperazinyl}butyl]-bicyclo[2.2.2]octane-2,3-dicarboximide or a pharmaceutically acceptable acid addition salt thereof.

6. A pharmaceutical composition which comprises as an active ingredient a pharmaceutically effective amount of at least one of the compounds claimed in claim 1 and at least one pharmaceutically acceptable inert carrier or diluent.

7. A pharmaceutical composition which comprises as an active ingredient a pharmaceutically effective amount of the succinimide derivative of claim 3, and at least one pharmaceutically acceptable inert carrier or diluent.

8. A method for reducing anxiety, comprising:
administering an effective anxiety reducing amount of the composition of claim 6 to a subject.

9. A method for reducing anxiety, comprising:
administering an effective anxiety reducing amount of the composition of claim 7 to a subject.

* * * * *